United States Patent [19]

Tolman et al.

[11] Patent Number: 4,994,464
[45] Date of Patent: Feb. 19, 1991

[54] PIPERAZINYLPYRIMIDINES AS β-ADRENERGIC RECEPTOR BLOCKERS

[75] Inventors: Richard L. Tolman, Warren, N.J.; John J. Baldwin, Gwynedd Valley, Pa.; Arthur F. Wagner, Princeton, N.J.; Adolph Pietruszkiewicz, North Wales, Pa.

[73] Assignee: Merck & Co., Inc., Rahway, N.J.

[21] Appl. No.: 417,535

[22] Filed: Oct. 5, 1989

Related U.S. Application Data

[62] Division of Ser. No. 91,471, Aug. 31, 1987, Pat. No. 4,889,856.

[51] Int. Cl.$^5$ ............... C07D 495/04; A61K 31/505
[52] U.S. Cl. ..................... 514/254; 544/255; 544/278
[58] Field of Search ................ 544/255; 514/254

[56] References Cited

U.S. PATENT DOCUMENTS

| | | | |
|---|---|---|---|
| 3,272,811 | 9/1966 | Ohnacker et al. | 544/278 |
| 3,311,623 | 3/1967 | Ohnacker et al. | 544/255 |
| 3,318,881 | 5/1967 | Ohnacker et al. | 544/278 |
| 3,318,883 | 5/1967 | Ohnacker et al. | 544/278 |
| 4,889,856 | 12/1989 | Tolman et al. | 544/255 |

FOREIGN PATENT DOCUMENTS 724745  5/1969  Belgium .
2119368 11/1983  United Kingdom .

Primary Examiner—Mukund J. Shah
Assistant Examiner—F. Bernhardt
Attorney, Agent, or Firm—William H. Nicholson; Joseph F. DiPrima

[57] ABSTRACT

Certain piperazinylpyrimidines have pronounced β-adrenergic blocking properties and some of the compounds are particularly useful in the treatment of elevated intraocular pressure and glaucoma.

6 Claims, No Drawings

PIPERAZINYLPYRIMIDINES AS β-ADRENERGIC RECEPTOR BLOCKERS

This is a division of application Ser. No. 07/091,471, filed Aug. 31, 1987 (now U.S. Pat. No. 4,889,856).

SUMMARY OF THE INVENTION

This invention is concerned with compounds of structural formula.

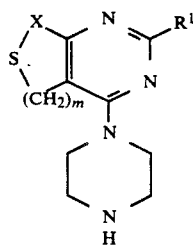

wherein X, m, and $R^1$ are as hereinafter defined which are β-adrenergic blocking agents some of which are especially useful in the treatment of elevated intraocular pressure and/or glaucoma because of a low degree of blockade of non-ocular β-receptors after topical administration.

The invention is also concerned with pharmaceutical formulations of the novel compounds; methods of treating hypertension, angina, migraine, arrhythmia and elevated intraocular pressure/glaucoma; and processes for preparing the compounds.

BACKGROUND OF THE INVENTION

Glaucoma is an ocular disorder associated with elevated ocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. A few β-adrenergic blocking agents are effective in reducing intraocular pressure. While many of these agents are effective in reducing intraocular pressure, they also have other characteristics, e.g. local anesthetic activity, that are not acceptable for chronic ocular use because of the potential for corneal damage, directly as the result of the anesthesia, or indirectly by the presence of foreign particles that may go unnoticed in the anesthetized eye.

Timolol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

However, known β-adrenergic blocking agents have not been shown to demonstrate any meaningful oculoselectivity and, in spite of the low dose normally required for ocular administration, manifest their β-blocking properties in extra ocular tissue, especially the pulmonary and cardiovascular systems to such an extent that they should not be administered to patients with pulmonary or cardiovascular ailments.

With this invention β-adrenergic blocking properties have been discovered in a type of chemical structure not previously known to exhibit such properties and quite different from the traditional β-blockers all or most of which have a 3-amino- 2-hydroxypropoxy or similar group.

The general type of chemical structure of the novel compounds of this invention is known.

Certain 6$\underline{H}$-7,8-dihydrothiopyrano[3,2-d]-pyrimidines are disclosed in Belgian Patent No. 724745 as intermediates for the preparation of compounds with cardiovascular and coronary dilation activity, however, no suggestion is made of any β-blocking activity for either the intermediates or the final products. Great Britain 2119368 discloses 6$\underline{H}$-7,8-dihydrothiopyrano[3,2-d]pyrimidines with a very different substitution pattern on the nucleus when compared with the instant compounds. U.S. Pat. Nos. 3,318,883, 3,272,811, and 3,318,881 disclose dihydrothieno[3,2-d]pyrimidines.

Now, with the present invention there are provided compounds of similar structure with pronounced β-blocking properties, some of which are oculoselective having little or no liability by way of local anesthesia or extra-ocular β-blocking activity; pharmaceutical formulations of those compounds; methods of treating hypertension and elevated intraocular pressure with certain of these compounds; and processes for preparation of these compounds.

The principal difference between the claimed compounds and the compounds of the above references is that the claimed compounds have a hydrogen on the piperazine nitrogen and superior β-blocking activity to the reference compounds which have a substituent such as alkyl, benzyl, cyclopropyl or the like on the piperazine nitrogen, as shown in the following table:

TABLE

| R¹ | R² | Concentration (nM) To Block Binding of Ligand by 50% | |
|---|---|---|---|
| | | $\beta_1$ | $\beta_2$ |

[Structure 1: tetrahydrobenzothiophene-pyrimidine with piperazine-N-R² and R¹ substituent]

| R¹ | R² | $\beta_1$ | $\beta_2$ |
|---|---|---|---|
| —CH₃ | H | 680 | 314 |
| —C₆H₅ | H | 290 | 73 |
| —CH₂C₆H₅ | H | 479 | 242 |
| cyclopropyl | H | 590 | 73 |
| —CH₃ | —CH₂C₆H₅ | 0% @ 10,000 (1) | 0% @ 10,000 (1) |
| —CH₃ | —C₂H₅ | 3% @ 10,000 (1) | 27,000 |
| —CH₃ | cyclopropyl | 6% @ 10,000 (1) | 8% @ 10,000 (1) |
| —C₄H₉-n | —CH₃ | 4,300 | 4,800 |
| —C₂H₄OH | —CH₃ | 7% @ 10,000 (1) | 14% @ 10,000 (1) |

[Structure 2: tetrahydrothienopyrimidine variant with piperazine-N-R²]

| R¹ | R² | $\beta_1$ | $\beta_2$ |
|---|---|---|---|
| —CH₃ | H | 820 | 340 |
| —CH₃ | —CH₃ | 15% @ 10,000 (1) | 24% @ 10,000 (1) |

[Structure 3: thienopyrimidine with piperazine-N-R²]

| R¹ | R² | $\beta_1$ | $\beta_2$ |
|---|---|---|---|
| —C₂H₅ | H | 300 | 140 |
| —C₂H₅ | CH₃ | 2,403 | 1,042 |

(1) % blocked at nM concentration shown; 50% blockade not achieved at reasonable concentrations.

DETAILED DESCRIPTION OF THE INVENTION

The novel compounds of this invention have structural formula:

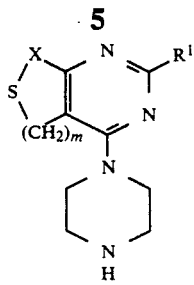

or a pharmacologically acceptable salt thereof, wherein:

X is $(CH_2)_{1-3}$, —CH=CH— OR —$CH_2SCH_2$— m is 0 or 1; and $R^1$ is
- (1) hydrogen,
- (2) $C_{1-5}$alkyl, straight or branched and either unsubstituted or substituted with
  - (a) cyano,
  - (b) phenyl-$C_{1-5}$alkoxy,
  - (c) phenyl,
  - (d) $C_{1-3}$alkoxy,
- (3) $C_{1-5}$alkylthio,
- (4) halo, such as chloro, fluoro or bromo,
- (5) phenyl, either unsubstituted or substituted with one or more of
  - (a) nitro
  - (b) halo, such as chloro, bromo or fluoro,
  - (c) $C_{1-3}$alkyl, or
  - (d) $C_{1-3}$alkoxy,
- (6) $C_{3-6}$-cycloalkyl, or
- (7) heteroaryl, such as pyridyl, imidazolyl, pyrimidinyl, or pyrazinyl.

For ophthalmic use in the treatment of elevated intraocular pressure and/or glaucoma, it is preferred that $R_1$ be $C_{3-6}$ cycloalkyl, especially cyclopropyl, $C_{1-5}$alkyl, or $C_{1-5}$alkylthio.

The pharmacologically acceptable salts of the compounds of this invention include those formed from inorganic acids such as hydrochloric, sulfuric and phosphoric acids and those formed from organic acids such as maleic acid, 2-naphthalenesulfonic acid, 3,5-di-tert butylsalicylic acid, 2-chloro-4,6-disulfamoylphenol, 2,5-dihydroxybenzoic acid (gentisic acid), citric acid, pamoic acid, pyruvic acid, isethionic acid, fumaric acid or the like.

Ophthalmic formulations comprising one or more of the compounds of this sub-genus of the novel compounds forms another embodiment of this invention. The ophthalmic composition of this invention may be in the form of a solution, suspension, ointment, gel, solid insert or a solution which gels on ocular administration, such as one containing a gelan gum type of polysaccharide and contains about 0.01 to 5% and especially about 0.5 to 2% by weight of medicament. Higher concentrations as, for example about 10% or lower concentration can be employed. It may be employed as the sole active ingredient or in combination with other β-blockers, such as timolol maleate; a parasympathomimetic agent such as pilocarpine, or a topically effective carbonic anhydrase inhibitor. The agents would be employed in approximately equal amounts.

A unit dose comprises about 0.001 to 5.0 mg, preferably about 0.005 to 2.0 mg, and especially about 0.05 to 1.0 mg of active compound per eye. Multiple unit doses are administered as needed to achieve and maintain a normotensive or close to normotensive ocular condition.

The β-adrenergic blocking properties of the novel compounds of this invention indicate that they are also useful in the treatment of conditions such as hypertension, angina pectoris, or certain arrhythmias which are known to be amenable to treatment with β-adrenergic blocking agents.

For use as extra-ocular β-adrenergic blocking agents, the present compounds can be administered orally, transdermally, or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches, and other carriers; as liquids dissolved or dispersed or emulsified in a suitable liquid carrier; in capsules encapsulated in a suitable encapsulating material; or (b) for parenteral administration dissolved or dispersed in a suitable liquid carrier such as solution or as an emulsion, or (c) as an aerosol or patch for transdermal administration. The ratio of active compound to compounding ingredients; i.e., carrier, diluent, etc., will vary as the dosage form requires. Generally, doses of the present compounds of from about 0.01 to about 50 mg/kg and preferably from about 0.1 to about 20 mg/kg of body weight per day may be used. Dosage may be single or multiple depending on the daily total required and the unit dosage.

The novel compounds are prepared from $R^1$-substituted-4-chloro pyrimidines IV, by treatment with piperazine or N-protected piperazine, in accordance with the following reaction scheme which also shows synthesis of compound IV.

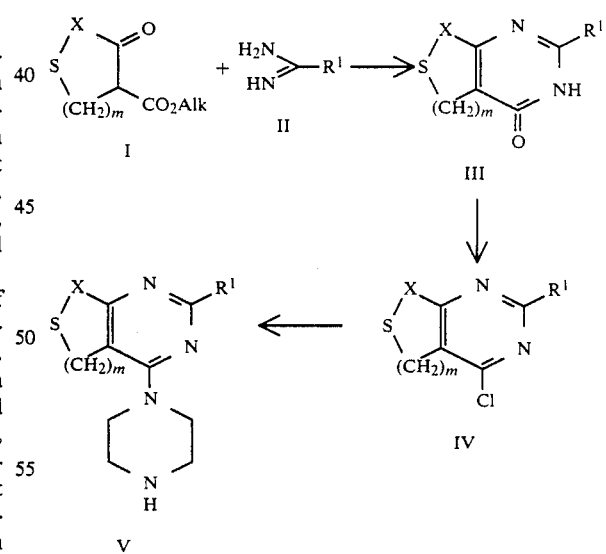

wherein $R_1$ is as defined above.

In the first step of the above reaction scheme, a compound of formula I is reacted with an $R^1$-substituted amidine (II). The free base of the amidine is usually employed which is usually generated in situ by treating an amidine salt with a strong base. While any base that is a stronger base than the amidine itself may be used, generally an alkali metal base, such as sodium or potassium alkoxide is preferred. The solvent is generally a solvent compatible with the base and it is thus generally preferred to use an alcohol which corresponds to the alkoxide base used, such as methanol or ethanol. Sodium methoxide in methanol is the preferred solvent system and base. The amidine free base is then combined with compound I to prepare the 2-$R^1$-substituted pyrimidine-4-one (III). The reaction is carried out at from 0° C. to the reflux temperature of the reaction mixture and is generally complete in from 30 minutes to 24 hours. It is preferred to carry out the reaction at about room temperature. The product is isolated using techniques known to those skilled in the art with the product generally not being purified but rather used directly in the next step.

Compound III is then reacted with a chlorinating agent such as phosphorus oxychloride, thionyl chloride or the like. While a solvent may be employed it is generally preferred to use the chlorinating agent in excess and to dispense with the use of a solvent. Generally the reaction is heated to at least 50° C. up to the reflux temperature of the reaction mixture for from about 1 hour to 3 days. It is preferred to use phosphorus oxychloride as the chlorinating agent and to heat it at about 100° C. overnight. The chlorinated compound (IV) is isolated using known techniques.

Compound V is prepared from the 4-chloro compound (IV) by displacing the chlorine with piperazine, or N-protected piperazines such as 1-piperazinecarboxaldehyde, or N-t-butoxycarbonylpiperazine.

The reaction employing piperazine is carried out preferably in an unreactive alcohol solvent although any solvent which does not react with compound IV or the amine is suitable such as ethers, THF, DMF, benzene, or the like. The reaction is carried out at elevated temperatures of from 80° to 150° C. and is generally complete in from 3 to 24 hours. It is preferred to heat the reaction at from 100°-120° C. in an alcohol solvent with a boiling point in excess of the reaction temperature. Thus, isoamyl alcohol with a boiling point of 132° C. is a preferred solvent.

Generally the piperazine reactant is used in excess with at least 2 and preferably 3 or more molar equivalents in order to provide a scavenger for the hydrogen chloride liberated during the course of the reaction. Alternatively, a single molar equivalent may be used along with a tertiary amine such as triethylamine or pyridine to act as the scavenger for the hydrogen chloride. The products are purified using standard techniques, and are preferably isolated as the acid addition or other physiologically acceptable salt such as the hydrochloride, nitrate, sulfate, maleate, citrate, and the like.

In syntheses of Compound V using 1-piperazinecarboxaldehyde, it is mixed with the appropriate 4-chloro compound (IV) in acetonitrile and refluxed for 10-24 hours, usually about 16 hours. After removal of the solvent, the residue is heated with dilute HCl at about 75° C. to reflux for about 0.5 to 2 hours.

The preparations employing N-t-butoxycarbonylpiperazine are conducted in a high boiling alcohol such as isoamyl alcohol at about reflux temperature for about 0.5 to 2 hours. After removal of the solvent, the residue is treated at about room temperature with an acid such as trifluoroacetic acid for about 1 hour to provide the final product.

EXAMPLE 1

2-Cyclopropyl-7,8-dihydro-4-(1-piperazinyl)-6H-thiopyrano[3,2-d]pyrimidine dihydrochloride hemihydrate Step A: Preparation of 2-Cyclopropyl-7,8-dihydro-4-hydroxy-6H-thiopyrano[3,2d]pyrimidine Sodium metal (3.94 g, 0.17 g atom) was dissolved in methanol (150 ml) and cyclopropylcarboxamidine hydrochloride (21.0 g, 0.174 mol) was added followed after ¼ hour stirring by the addition of ethyl 3-oxotetrahydrothiopyran-2-carboxylate (27.2 g, 0.145 mol). The reaction mixture was stirred at 25° C. for 18 hours then treated with ice water (200 ml) and neutralized with acetic acid to give 24.6 g of the title compound which melted at 249°-250° C.

Step B: Preparation of 2-Cyclopropyl-4-chloro-7,8-dihydro-6H-thiopyrano[3,2-d]pyrimidine A stirred solution of product from Step A (17 g) in phosphorus oxychloride (160 ml) was heated at reflux for 1 hour. Two-thirds of the phosphorus oxychloride was distilled from the reaction mixture and the residue poured into ice water to give 12.1 g of title compound which was dried and used in Step C without further purification or characterization.

Step C: Preparation of 2-Cyclopropyl-7,8-dihydro-4-(1-piperazinyl)-6H-thiopyrano[3,2-d]pyrimidine dihydrochloride hemihydrate A solution of product from Step B (12.1 g), and 1-piperazinecarboxaldehyde (11 ml) in acetonitrile (15 ml) was heated at reflux for 16 hours. The acetonitrile was distilled at reduced pressure and the gummy residue treated with H$_2$O (280ml) and concentrated hydrochloric acid (70 ml) and heated at 95° C. for 1 hour. The solvent was distilled at reduced pressure, the residue treated with ammonium hydroxide, extracted with CH$_2$Cl$_2$ washed with water, brine and dried over K$_2$CO$_3$. The CH$_2$Cl$_2$ was distilled at reduced pressure and the residue chromatographed on silica gel (320 g) eluting with CHCl$_3$.CH$_3$OH (9:1). The pertinent fractions were combined and evaporated, the product dissolved in ethanol (60 ml), treated with 10N sthanolic HCl (10 ml) and ether (60 ml) to give 12.5 g of title compound which melted at 205°-207° C. after recrystallization from ethanol-ether.

Analysis for C$_{14}$H$_{20}$ON$_4$S.2HCl.½H$_2$O Calc: C, 46.92; H, 6.47; N, 15.64; Found: C, 46,81; H, 6.61; N, 15.24.

Employing the procedure substantially as described in Example 1, Steps, A, B and C, but substituting for the cyclopropylcarboxamidine hydrochloride used in Step A thereof, an equimolecular amount of the hydrochloride of an amidine of formula

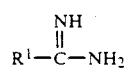

there are produced the 2-$R^1$-4-(1-piperazinyl)-7,8-dihydro-6H-thiopyrano[3,2-d]pyrimidines described in Table I in accordance with the following reaction scheme:

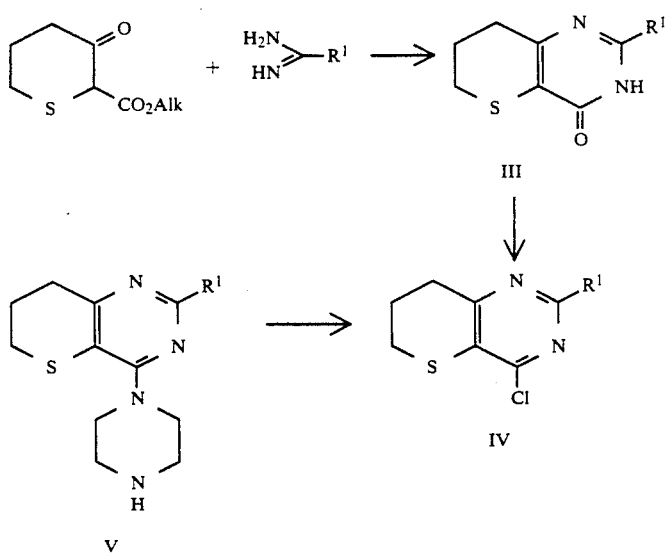

TABLE I

| R[1] | m.p. (°C.) Compound III | IV | V |
|---|---|---|---|
| —CH(CH$_3$)$_2$ | 229–231 | not purified | See Example 2 |
| 3-NO$_2$-phenyl | — | — | >300 (HCl) |
| 4-pyridyl | 293–295 (dec.) | — | >280 (maleate hemiisopropanolate) |
| —C$_2$H$_5$ | — | — | >275 (2 HCl″ H$_2$O) |
| —CH$_2$-phenyl | — | — | >250 (2 HCl) |
| phenyl | 264–266 (dec.) | — | 182–184 (2 HCl″0.5 H$_2$O) |
| H | — | — | *(2 HCl) |
| —CH$_3$ | — | — | *(2 HCl″9/10 C$_2$H$_5$OH″1/10 H$_2$O) |
| —CH$_2$CH$_2$CH$_3$ | — | — | *(2 HCl) |
| —SCH$_3$ | — | — | 153–155° C. (2 HCl) |

*characterized by mass spec. and n.m.r.

EXAMPLE 2

7,8-Dihydro-2-(1-methylethyl)-4-(1-piperazinyl)-6H-thiopyrano[3,2-d]pyrimidine dihydrochloride hemisemihydrate

A solution of 4-chloro-7,8-dihydro-2-(1-methylethyl)-6H-thiopyrano[3,2-d]pyrimidine (from Table I) (2.8 g) and N-tert-butoxycarbonylpiperazine (5.0 g) in isoamyl alcohol (50 ml) was heated at reflux for 1 hour, cooled, filtered and the solvent distilled at reduced pressure. The residue was dissolved in ether, washed with H$_2$O and brine, dried over magnesium sulfate and evaporated in vacuo. To the residue was added trifluoroacetic acid (40 ml) which after 1 hour was distilled at reduced pressure. The residue was treated with ice and excess 10N sodium hydroxide, extracted into CH$_2$Cl$_2$, washed with water and brine and dried over K$_2$CO$_3$. The CH$_2$Cl$_2$ was distilled at reduced pressure and the residue was dissolved in ethanol (30 ml), treated with 10N ethanolic HCl (3 ml) and ether (30 ml) to give the title compound which melts at 256° to 258° C. after recrystallization from 2-propanol-ether.

Anal. Calc'd for $C_{14}H_{22}N_4S \cdot 2HCl \cdot \frac{1}{4}H_2O$ C, 47.25; H, 6.94; N, 15.74; Found: C, 47.32; H, 7.24; N, 15.69.

Similarly prepared were: 7,8-dihydro-2-methyl-4-(2-methyl-1-piperazinyl)-6H-thiopyrano[3,2-d]pyrimidine dihydrochloride, M/e=264.

Anal. Calc'd for $C_{13}H_{22}Cl_2N_4S \cdot O.26\ H_2O$ (341.99): H, 16.39; C, 45.65; H, 6.64; Cl, 20.73; S, 9.37. Found: N, 16.39; C, 45.57; H, 6.48; Cl, 21.23; S, 10.08; and 7,8-dihydro-2-n-propyl-4-(1-piperazinyl)-6H-thiopyrano[3,2-d]pyrimidine dihydrochloride, M/e 278.

Anal. Calc'd for $C_{14}H_{24}Cl_2N_4S$(351.33): N, 15.95; C, 47.86; H, 6.89; Cl, 20.18; S, 9.13. Found: N, 15.52; C, 47.64; H, 6.61; Cl, 20.08; S, 8.82.

EXAMPLE 3

7,8-dihydro-2-Methoxymethyl-4-(1-piperazinyl)-6H-thiopyrano[3,2-d]pyrimidine dihydrochloride hydrate Step A: Preparation 2-chloromethyl-7,8-dihydro-4-hydroxy-6H-thiopyrano[3,2-d]pyrimidine Sodium carbonate (1 4 g) was dissolved in 20 ml of water and chloromethylcarboxamidine hydrochloride (1.19 g, 0.01 mol) was added followed by ethyl 3-oxotetrahydrothiopyran-2-carboxylate (1.6 g, 0.01 mol). After 2 hours of stirring at 25° C. a gray solid was recovered by filtration, recrystallization from ethanol gave 0.7 g of title compound which melted at 233°-235° C.(dec).

Anal. Calc'd for $C_8H_9N_2OClS$: Calc: C, 44.34; H, 4.19; N, 12.99; Found: C, 44.57; H, 4.50; N, 13 40.

Step B: Preparation of 7,8-dihydro-4-hydroxy-2-Methoxymethyl-6H-thiopyrano[3,2-d]pyrimidine Sodium metal (0.46 g, 0.02 gr. atm.), was dissolved in methanol (I00 ml) and the product from step A was added. The reaction mixture was refluxed for 4 hours and then most of the solvent was removed in vacuo. The addition of water afforded 1.2 g of title compound which was dried and used in step C without further purification Step C: Preparation of 4-chloro-7,8-dihydro-2-Methoxymethyl-6H-thiopyrano[3,2-d]pyrimidine The title compound was prepared following substantially the same procedure described in Example 1, step B using the product from step B of this Example 3 and phosphorus oxychloride. This procedure gave 1.0 g of title compound which was dried and used in step D without further purification.

Step D: Preparation of 7,8-dihydro-2-Methoxymethyl-6H-4-(1-piperazinyl)thiopyrano[3,2-d]pyrimidine dihydrochloride hydrate The title compound was prepared following substantially the same procedure described in Example 1, step C, using the following substances:

| The title compound from step C | 1.0 g, 0.005 mol |
| 1-piperazinecarboxaldehyde | 3 excess |
| acetonitrile | 25 ml |
| 2N HCl | 20 ml. |

This procedure gave 0.5 g (from isopropanol) of material which melts at 140°-143° C.

Analysis for $C_{13}H_{20}N_4OS \cdot 2HCl \cdot H_2O$: Calc: C, 42.05; H, 6.79; N, 15.09; Found: C, 41.85; H, 6.84; N, 15.41.

EXAMPLE 4

2-Cyanomethyl-7,8-dihydro-4-(1-piperazinyl)-6H-thiopyrano[3,2-d]pyrimidine maleate Step A: Preparation 2-cyanomethyl-7,8-dihydro-4-hydroxy-6H-thiopyrano[3,2-d]pyrimidine Product from Example 3, step A, (1.8 g, 0.01 mol) was dissolved in 10 ml of DMSO and sodium cyanide (1.0 g) was added. The reaction mixture was stirred at 25° C. for 3.5 hours and then poured into water (150 ml). The solution was extracted with ethyl acetate, the ethyl acetate was dried and then evaporated to give the title compound as an oil that was used directly in Step B hereof.

Step B: Preparation of 4-chloro-2-cyanomethyl-7,8-dihydro-6H-thiopyrano[3,2-d]pyrimidine The title compound was prepared following substantially the same procedure described in Example 1, Step B using the product from Step A and phosphorus oxychloride. This procedure gave 1.2 g of product as a brown granular solid which was used in the next step.

Step C: Preparation of 2-Cyanomethyl-7,8-dihydro-4-(1-piperazinyl)-6H-thiopyrano[3,2-d]pyrimidine maleate The title compound was prepared following substantially the same procedure described in Example 1, Step C using the following substances:

| product from Step B | 1.2 g |
| 1-piperazinecarboxaldehyde | 4 g (excess) |
| acetonitrile | 25 ml |
| 2N HCl | 20 ml |

This procedure gave 1.0 g of product which was converted to the maleate salt and crystallized from isopropanol to afford 0.5 g of title compound melting at 138°-140° C.

Anal. Calc. for $C_{17}H_{21}N_5O_4S$: Calc: C, 52.16; H, 5.41; N, 17 89; Found: C, 52.08; H, 5.51; N, 17.88.

EXAMPLE 5

2-Benzyloxymethyl-7,8-dihydro-4-(1-piperazinyl)-6H-thiopyrano[3,2-d]pyrimidine dihydrochloride hemihydrate Step A: Preparation of 2-Benzyloxymethyl-7,8-dihydro-4-hydroxy-6H-thiopyrano[3,2-d]pyrimidine Sodium hydride (0.68 g 53% mineral oil) was suspended in THF (80 ml) and 1.5 ml of benzyl alcohol was added dropwise with stirring. To this clear solution was added product from Example 3, Step A (2.6 g) dissolved in 25 ml of DMF. After stirring for 2 hours at 25° C. the reaction mixture was heated at reflux for 10 minutes. The solvent was removed in vacuo, water was added to the residue followed by enough diluted HCl to render the solution slightly acidic and it was extracted with ethyl acetate. The ethyl acetate layer was dried and evaporated to give title compound as an oil that was used directly in Step B.

Step B: Preparation of 2-Benzyloxymethyl-7,8-dihydro-4-chloro-6H-thiopyrano[3,2-d]pyrimidine The title compound was prepared following substantially the same procedure described in Example 1, Step B using the title compound from Step A hereof and phosphorus oxychloride. The procedure gave 0.8 gm of product as a brown solid which was used in Step C without further purification.

13

Step C: Preparation of 2-Benzyloxymethyl-7,8-dihydro-4-(1-piperazinyl)thiopyrano[3,2-d]pyrimidine dihydrochloride hemihydrate The title compound was prepared following substantially the same procedure as described in Example 1, Step C using the following substances:

| Product from step B, hereof | 0.8 g |
|---|---|
| 1-piperazinecarboxaldehyde | 3 g (excess) |
| acetonitrile | 25 ml |
| 2N HCl | 20 ml |

This procedure gave 0.3 g of title compound (from isopropanol) which melts 108°-110° C.

Anal. Calc'd for $C_{19}H_{24}N_4OS.2HCl.0.5H_2O$ C, 52.05; H, 6.21; N, 12.78; Found: C, 52.22; H, 6.71; N, 13.01.

EXAMPLE 6

7,8-dihydro-2-methyl-4-(1-piperazinyl)-6H-thiopyrano[3,2-d]pyrimidine dihydrochloride A solution of 4-chloro-7,8-dihydro-2-methyl-6H-thiopyrano[3,2-d]pyrimidine in isoamyl alcohol (1 mmol/4 ml) was added dropwise over about 1 hour to 4 equivalents of piperazine in isoamyl alcohol (1 mmol/5 ml) at 100° C. After the chloroheterocycle had disappeared (tlc), about 4–18 hours, the mixture was concentrated under reduced pressure and the residue was partitioned between a chloroform water system at pH 10–11 (NaOH). The chloroform extract was concentrated to dryness under reduced pressure. The residue was chromotographed on silica gel with 5% methanol in chloroform and was converted to the dihydrochloride which was isolated in 77% yield after recrystallization from ethanol. M/e=250.

Anal. Calc'd for $C_{12}H_{20}Cl_2 N_4S.0.6C_2H_5OH.1.1 H_2O$ (370.74): N, 15.12; C, 42.76; H, 7.01; Cl, 19.12, S, 8.65. Found: N, 15.28; C, 42 42; H, 6.50; Cl, 18-84; S, 8 41.

EXAMPLE 7

2-Chloro-7,8-dihydro-4-(1-piperazinyl)-6H-thiopyrano[3,2-d]pyrimidine maleate

To a solution of piperazine (10.8 g., 0.125 mol) in 100 ml of chloroform at 0° C. was added a solution of 2,4-dichloro-7,8-dihydro-6H-thiopyrano[3,2-d]pyrimidine(6.6 g., 0.03 mol) in 20 ml of chloroform over 15 minutes at 0° C. After stirring at 0° C. for 16 hour, the mixture was extracted with 100 ml of 5% aqueous sodium bicarbonate, dried over magnesium sulfate and concentrated in vacuo. Trituration of the oil with diethyl ether gave crystals (5.4 g., 0.020 Mol) with m.p. 89°-91°.

A mixture of 82 mg (0.30 mMol) of the free base and 70 mg. (0.60 mMol) of maleic acid was dissolved in 2 ml of methanol. After a few minutes, the salt which separated was collected to yield 74 mg. (0.20 mmol) of 2-chloro-7,8-dihydro-4-(1-piperazinyl)-6H-thiopyrano[3,2-d]pipyridine maleate, m.p. 188°-189°.

Anal. Calc'd for $C_{11}H_{15}N_4SCl.C_4H_4O_4$ (386.88): C, 46.57; H, 4.95; N, 14.48; S, 8.29; Cl, 9.07. Found: C, 46.81; H, 4.99; N, 14.78; S, 8.56; Cl, 9.07.

EXAMPLE 8

7,8-Dihydro-2-ethyl-4-(1-piperazinyl)-6H-thiopyrano[3,2-d]pyrimidine dihydrochloride A solution (1 mmole/3 ml) of 4-chloro-7,8-dihydro-2-ethyl-6H-thiopyrano[3,2-d]pyrimidine in benzene was mixed with a four-fold molar excess of piperazine in benzene (1 mmole/ml) and the reaction mixture was heated to reflux. Within an hour piperazine hydrochloride began to precipitate. The reaction was monitored by tlc for disappearance of starting chloroheterocycle. After the chloroheterocycle was consumed, the reaction mixture was filtered and the benzene phase was concentrated to dryness. The residue was taken up in a chloroform-water system in which the pH was adjusted to 10–11 with sodium hydroxide. The chloroform extract was washed with saturated brine, dried over anhydrous magnesium sulfate and concentrated to dryness under reduced pressure. The product was converted to the dihydrochloride with a slight excess of 2N hydrochloric acid or anhydrous hydrogen chloride in ethanol. The salt which crystallized from ethanol was obtained in 45% yield.

Anal. Calc'd for $C_{13}H_{22}Cl_2H_4S.0.2 C_2 H_5OH.0.25 H_2O$ (351.03): N, 15.96; C, 45.85; H, 6.81; Cl, 20.20. Found: N, 16.19; C, 45.48; H, 6.77; Cl, 19 77.

Similarly prepared was 2-benzyl-7,8-dihydro-4-(1-piperazinyl)-6H-thiopyrano[3,2-d]pyrimidine dihydrochloride; M/e=326.

Anal. Calc'd for $C_{18}H_{24}Cl_2N_4S$ (399.37): N, 14.03; C, 54.13; H, 6.06; Cl 17.75; S, 8.03. Found: N, 14.10; C, 53.86; H, 6.25; Cl 17.56; S, 7.76.

EXAMPLE 9

2-Ethyl-4-(1-piperazinyl)thieno[3,2-d]pyrimidine dihydrochloride

Step A: Preparation of 2-Ethyl-4-hydroxythieno[3,2-d]pyrimidine

Methyl 3-amino-2-thiophenecarboxylate (4.67 g,) and propionamidine (3 g, were combined and heated in an oil both for ½ hour at 60° C.; ½ hour at 80° C.; ½ hour at 100° C. and finally for 4 hours at 120° C. The mixture was cooled, triturated with ether, filtered and washed with ether to obtain 0.67 g of the product; m.p. 233°-237° C.

Step B: Preparation of 4-Chloro-2-ethylthieno[3,2-d]pyrimidine

2-Ethyl-4-hydroxythieno[3,2-d]pyrimidine (0.6725 g, 0.00373M) was refluxed with phosphorus oxychloride (20 ml) for 2 hours. The reaction mixture was cooled, concentrated under vacuum, the residue dissolved in methylene chloride, poured over ice and water and basified with ammonia. The layers were separated and the aqueous layer extracted with ether. The combined organic extracts were washed with brine, dried (MgSO$_4$) and concentrated under vacuum to obtain the product, 0.65 g, as a tan solid, m.p. 46°-48° C. the structure of which was confirmed by NMR.

Step C: Preparation of 2-Ethyl-4-(1-piperazinyl)-thieno[3,2-d]pyrimidine dihydrochloride 4-Chloro-2-ethylthieno[3,2-d]pyrimidine (0.65 g, 0.00327M) was refluxed with 1-t-butoxycarbonylpiperazine (1.83 g, 0.0098M) in isoamyl alcohol (12 ml) for 2 hours. The reaction mixture was cooled, diluted with 150 ml of equal volumes of ether and hexane, filtered and the filtrate concentrated under vacuum. The residue was chromatographed on silica eluting with ethyl acetate-hexane 1:1. The product fractions on concentration gave a colorless solid, 1.04 g, m.p. 117°-119° C. which was added to trifluoroacetic acid, 20 ml at 25° C. After stirring 1½ hours, the mixture was concentrated and the residue was taken up in dilute sodium hydroxide and ether. The layers were separated, the aqueous layer extracted with methylene chloride; the combined organic extracts were washed with brine, dried (MgSO₄) and concentrated. The residue was chromatographed on silica eluting with THF/NH₄OH (40/1). The product fractions were concentrated under vacuum to obtain the free base of the product, 0.66 g. On acidification of an ethereal solution with ethanolic HCl, the dihydrochloride separated, m.p. 290°–295° C.

Employing the procedure substantially as described in Example 9, Steps A to C, but substituting for the propionamidine used in Step A thereof an amidine of formula R¹C (=NH) NH₂ described in Table II, there are produced the 2-R¹-4-(1-piperazinyl)thieno[3,2,-d]pyrimidines, also described in Table II.

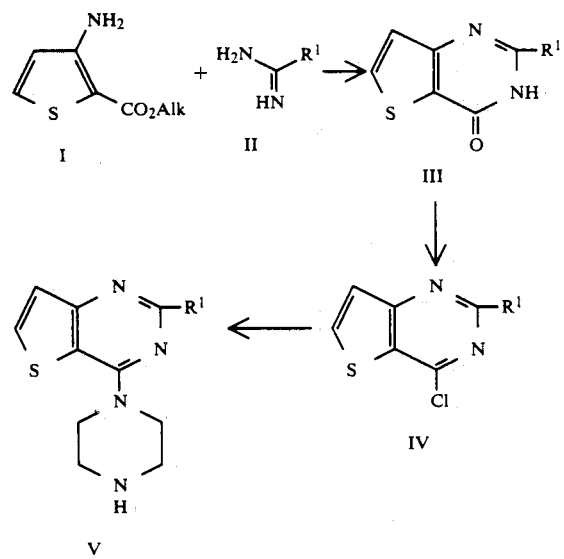

TABLE II

| R¹ | m.p. (°C.) Compound III | IV | V |
|---|---|---|---|
| —CH₂—C₆H₅ | | 268–272 (d) | 272–276 (d) (2 HCl.0.5 H₂O) |
| —C₆H₅ | | 116–118 | 260–265 (1) |
| —◁ | 258–260 | 62–64 | 240–244 (d) (2 HCl) |
| H | | | 148–154 (d) (1½maleate) |

(1) 2HCl.0.5H₂O.0.1C₂H₅OH.0.1 (C₂H₅)₂O solvate.

EXAMPLE 10

2-Ethyl-4-(1-piperazinyl)dihydrothieno[3,2-d]pyrimidine dihydrochloride

Step A: Preparation of 2-Ethyl-4-hydroxy-dihydrothieno [3,2-d]pyrimidine

Propionamidine hydrochloride (7.60 g, 0.07M) was added to a solution of sodium methoxide (7.56 g, 0.14M) in methanol (35 ml) at 25° C. The suspension was cooled with stirring to 3° C. and a mixture of methyl 3-ketotetrahydrothiophene-2-carboxylate and methyl 4-ketotetrahydrothiophene-3-carboxylate (11.21 g, 0.07M) (JACS, 68, 2229) in methanol (15 ml) was added over 15 minutes at 3° to 6° C. The mixture was stirred at 5° C. for 1 hour, then at 25° C. for 1½ hour and finally refluxed for 3 hours and cooled. Acetic acid (10 ml) was added and the suspension was concentrated under vacuum. The residue was triturated with water (50 ml) and the solid was filtered and washed on the funnel with water (3×15 ml), then ether.

The aqueous filtrate was extracted with four 75 ml portions of chloroform. The organic extracts were washed once with brine, dried (MgSO₄) and concentrated under vacuum. The residual oil was diluted with ether (15 ml) and hexane (15 ml). The solid that crystallized was filtered, washed with four 3 ml portions of other and combined with the solid obtained earlier from the aqueous solution. The 2.3 g of colorless solid was shown by NMR in DMSO to be a 1:1 mixture of 2-ethyl-4-hydroxy-dihydrothieno-[3,2-d]pyrimidine and 2-ethyl-4-hydroxy-dihydrothieno-[3,4-d]pyrimidine.

Step B: Preparation of 4-Chloro-2-ethyl-dihydrothieno [3,2-d]pyrimidine

A mixture of 2.25 g of 2-ethyl-4-hydroxydihydrothieno[3,2-d]pyrimidine and 2-ethyl-4-hydroxydihydrothieno[3,4-d]pyrimidine in phosphorus oxychloride (50 ml) was refluxed for 2 hours then cooled and concentrated under vacuum. The residue was dissolved in chloroform and poured into ice water. The mixture was basified with ammonia. The layers were separated and the aqueous phase extracted with chloroform. The combined organic extracts were washed with brine, dried (MgSO₄) and concentrated. The residual orange oil was chromatographed on 140 g of silica eluting with ethyl acetate/hexane (¼). Concentration of the first product fractions gave an oil, 1.05 g, shown by NMR to be 4-chloro-2-ethyldihydrothieno[3,4-d]pyrimidine. Concentration of the second product fractions gave an oil, 1.05 g, shown by NMR to be 4-chloro-2-ethyl-dihydrothieno-[3,2 d]pyrimidine.

Step C: Preparation of 2-Ethyl-4-(1-piperazinyl)dihydrothieno[3,2-d]pyrimidine dihydrochloride 4-Chloro-2-ethyl-dihydrothieno[3,2-d]pyrimidine (0.63 g, 0.00314M) was refluxed 1¾ hours with 1-t-butoxycarbonylpiperazine (2.05 g, 0.011M) in isoamyl alcohol (15 ml). The mixture was concentrated under vacuum; the residue was taken up in chloroform and washed with dilute potassium carbonate and water. The organic solution was dried (MgSO₄) and concentrated. The residue was chromatographed on silica eluting with ethyl acetate/hexane 1:1. The product fractions were concentrated to obtain 1.0 g of a colorless solid; m.p. 92°–94° C. This intermediate was stirred in trifluoroacetic acid (15 ml) for 1 hour and then the mixture was concentrated. The residue was taken up in water, basified with potassium carbonate and extracted with chloroform. The organic extracts were washed with water, dried (MgSO₄) and concentrated. The residual solid, 0.67 g, was dissolved in ethanol, filtered, diluted with ether and acidified with ethanolic HCl. The solid that deposited was filtered, washed with ether and dried at 100° C. under vacuum to obtain the product salt; m.p. 210°(d).

By similar procedures there was prepared 2-ethyl-4-[1-(4-methylpiperazinyl)]dihydrothieno [3,2-d]pyrimidine dihydrochloride, m.p. 267° C. (dec.); and 2-ethylthio-4-(1-piperazinyl) dihydrothieno [3,2-d]pyrimidine, m.p. 243° C. (dec.).

EXAMPLE 11

2-Cyclopropyl-4-(1-piperazinyl) dihydrothieno[3,4-d]pyrimidine dihydrochloride

Step A: Preparation of 2-Cyclopropyl-4-hydroxydihydrothieno[3,4-d]pyrimidine

Cyclopropylcarboxamidine hydrochloride (9.04 g, 0.075M) was added to a solution of sodium methoxide (4.05 g, 0.075M) in methanol (40 ml) at 15° C. with stirring. The suspension was cooled to 5° C. and methyl 4-ketotetrahydrothiophene-3-carboxylate (10.9 g, 0.068M) in methanol (10 ml) was added over ¾ hours. The mixture was stirred at 5° C. for 2 hours after addition and at 25° C. overnight then concentrated under vacuum. The residue was taken up in water, acidified with acetic acid (8 ml), and the product was filtered, washed with water and dried to obtain the crude product, m.p. 243°-246° C. (2.839) the structure of which was confirmed by NMR.

Step B: Preparation of 4-Chloro-2-cyclopropyldihydrothieno[3,4-d]pyrimidine

2-Cyclopropyl-4-hydroxydihydrothieno[3,4-d]pyrimidine (2.4 g, 0.0123M) was refluxed in phosphorus oxychloride (40 ml) for 1½ hours. The mixture was cooled, concentrated under vacuum, the residue dissolved in chloroform, poured over ice, and basified with ammonia. The layers were separated and the organic solution dried (MgSO$_4$) and concentrated. The residue, chromatographed on silica eluting with ethyl acetate/hexane, (1/6) gave 2.2 g of product, m.p. 86.5°-88.5° C. the structure of which was confirmed by NMR.

Step C: Preparation of 2-Cyclopropyl-4-(1-piperazinyl)-dihydrothieno[3,4-d]pyrimidine dihydrochloride 4-Chloro-2-cyclopropyldihydrothieno[3,4-d]pyrimidine (1.6 g, 0.0752M) was refluxed with 1-t-butoxycarbonylpiperazine (4.2 g, 0.0226M) in isoamyl alcohol (30M) for 1¾ hours. The mixture was cooled, concentrated and the residue dissolved in chloroform was washed with dilute sodium hydroxide, dried (MgSO$_4$) and concentrated. The residue chromatographed on silica eluting with ethyl acetate/hexane (6/10 v/v) yielded 2.5 g of solid m.p. 121°-123° C. which was then stirred in trifluoro acetic acid (30 ml) for 2 hours. The acid reaction mixture was concentrated, the residue dissolved in water, basified with sodium hydroxide and extracted with chloroform. The organic extracts were washed with water, dried (MgSO$_4$) and concentrated. The residue, (1.48 g) was dissolved in ether and the product salt obtained by acidification with ethanolic HCl and filtration, m.p. 247°-249° C. (dec.).

Employing the procedures substantially as described in Example 11 but starting with the appropriate carboxamidine in place of cyclopropylcarboxamidine, there are prepared: 2-phenyl-4-(1-piperazinyl)dihydrothieno[3,4-d]pyrimidine dihydrochloride hemihydrate, m.p. 208°-212° C. (dec.); 2-ethylthio-4-(1-piperazinyl)-dihydrothieno[3,4 d]pyrimidine maleate, m.p. 189° C. (dec.); and 2-methyl-4-(1-piperazinyl)dihydrothieno[3,4-d]pyrimidine dihydrochloride hemihydrate, m.p. 235° C. (dec).

EXAMPLE 12

6-Ethyl-8-[1-piperazinyl]-4H-m-dithiano[5,4-d]pyrimidine dihydrochloride

Step A: Preparation of 6-Ethyl-8hydroxy-4H-m-dithiano[5,4-d]pyrimidine

Propionamidine hydrochloride (3.82 g, 0.0352M) was added to a solution of sodium methoxide (1.9 g, 0.0352M) in ethanol (50 ml) at 20° C. with stirring. After 5 minutes 4-ethoxycarbonyl-5-m-dithianone (JACS, 82, 158, 1960) (6.19 g, 0.03M) was added. The suspension was stirred for 20 hours at 25° C., diluted with water, acidified with acetic acid, filtered, washed with water and dried to give 5.8 g. m.p. 268°-270° C. (dec.), characterized by NMR.

Step B: Preparation of 8-Chloro-6-ethyl-4H-m-dithiano[5,4-d]pyrimidine

6-Ethyl-8-hydroxy-4H-m-dithiano[5,4-d]pyrimidine (2.9 g, 0.01353M) was refluxed with phosphorus oxychloride (60 ml) for 2 hours. The reaction mixture was cooled, concentrated under vacuum, and the residue, dissolved in chloroform, was added to ice cold aqueous potassium carbonate. The layers were separated and the organic solution was washed with dilute ammonia, brine, then dried (MgSO$_4$) and concentrated. The residue was chromatograped on silica eluting with ethyl acetate/hexane, (1/5). The product fractions were concentrated to obtain 2.7 g, m.p. 68°-70° C. and characterized by NMR.

Step C: Preparation of 6-Ethyl-8-[1-piperazinyl]-4H-m-dithiano[5,4-d]pyrimidine dihydrochloride 8-Chloro-6-ethyl-4H-m-dithiano[5,4-d) pyrimidine (2.32 g, 0.01M) was refluxed with 1-t-butoxycarbonyl-piperazine (4.1 g, 0.022M) in isoamyl alcohol for 2 hours. The reaction mixture was cooled, diluted with CHCl$_3$ and washed with dilute potassium carbonate, water, dried (MgSO$_4$) and concentrated under vacuum. The residual oil was chromatographed on silica eluting with ethyl acetate/hexane, (35/120) to obtain 3.5 g of the protected piperazine, m.p. 105.5°-107.5° C. The intermediate was stirred in trifluoroacetic acid (40 ml) for 1½ hours at 25° C. and the mixture was then concentrated under vacuum. The residue was basified in aqueous potassium carbonate and extracted with chloroform. The organic extracts were washed with brine, dried (MgSO$_4$) and concentrated. The residue was dissolved in 60 ml of an equimolor mixture of ethanol and ether, filtered, diluted with ether, acidified with ethanolic HCl and filtered to obtain the hygroscopic product, m.p. 120°-125° C.

Using the procedures substantially as described in Example 12, but starting with cyclopropylcarboxamidine in place of propionamidine there were prepared in sequence 6-cyclopropyl-8-hydroxy-4H-m-dithiano[5,4-d]pyrimidine, m.p. 236°-287° C. (dec); 8-chloro-6-cyclopropyl-4H-m-dithiano[5,4-d]pyrimidine, m.p. 78°-80° C.; 6-cyclopropyl-8-(1-piperazinyl)-4H-m-dithiano[5,4-d]pyrimidine dihydrochloride, m.p. 135°-140° C. (dec.).

6-Methyl-8-(1-piperazinyl)-4H-m-dithiano[5,4-d]p yrimidinedihydrochloride, m.p. 215° C. was prepared similarly.

EXAMPLE 10

| Solution Composition | |
| --- | --- |
| 2-Cyclopropyl-7,8-dihydro-4-(1-piperzinyl)-6H-thiopyrano[3,2-d]pyrimidine dihydrochloride hemihydrate | 6.8 mg. |
| Sodium Chloride | 7.4 mg. |
| Benzalkonium chloride | 0.10 mg. |
| Soidium acetate anhydrous | 0.82 mg. |
| Water for injection q.s. and. | 1.0 ml. |

The active compound, salts, and benzalkonium chloride are added to and dissolved in water and the final solution diluted to volume. The solution is rendered sterile by filtration through a sterilizing filter.

EXAMPLE 11

| | |
|---|---|
| 7,8-Dihydro-2-(1-methylethyl)-4-(1-piperazinyl)-6H-thiopyrano-[3,2-d] pyrimidine dihydrochloride hemihydrate | 5 mg. |
| Petrolatum q.s. and. | 1 gram |

The active compound and the petrolatum are aseptically combined.

EXAMPLE 12

| | |
|---|---|
| 2-Cyclopropyl-7,8-dihydro-4-(1-piperzinyl)-6H-thiopyrano[3,2-d]pyrimidine dihydrochloride hemihydrate | 1 mg. |
| Hydroxypropylcellulose q.s. | 12 mg. |

Ophthalmic inserts are manufactured from compression molded films which are prepared on a Carver Press by subjecting the powder mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for ½ hour.

What is claimed is:

1. A compound of structural formula:

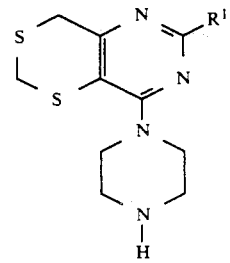

or an opthalmologically acceptable salt thereof, wherein:
$R^1$ is
(1) hydrogen,
(2) $C_{1-5}$alkyl, straight or branched and either unsubstituted or substituted with
(a) cyano,
(b) phenyl-$C_{1-5}$ alkoxy, or
(c) phenyl,
(3) phenyl, either unsubstituted or substituted with one or more of
(a) nitro
(b) halo,
(c) $C_{1-3}$alkyl, or
(d) $C_{1-3}$alkoxy,
(4) $C_{3-6}$ cycloalkyl.

2. The compound of claim 1, wherein $R^1$ is $C_{1-3}$alkyl or cyclopropyl, or an opthalmologically acceptable salt thereof.

3. The compound of claim 2 which is 6-ethyl-8-(1-piperazinyl)-4H-m-dithiano[5,4-d]pyrimidine.

4. An opthalmic formulation for the treatment of elevated intraocular pressure and glaucoma comprising an opthalmologically acceptable carrier and an effective intraocular pressure lowering and antiglaucoma amount of the compound of claim 1, or an opthalmologically acceptable salt thereof.

5. A method of treating elevated intraocular pressure and glaucoma which comprises the topical ocular administration to a patient in need of such treatment of an effective intraocular pressure lowering and antiglaucoma amount of the compound of claim 1 or an opthalmologically acceptable salt thereof.

6. A pharmaceutical formulation for the treatment of hypertension, angina, and arrhythmia comprising a pharmaceutically acceptable carrier and an effect antihypertensive, antiarrhythmic or antiangina amount of the compound of claim 1, or a pharmaceutically acceptable salt thereof.

* * * * *